United States Patent [19]

Simmonds

[11] 4,442,032
[45] Apr. 10, 1984

[54] ISOTHIOCYANATO-AZOBENZENE-SULFONIC, ARSONIC AND SUBSTITUTED-GLUTAMIC ACID HAPTENS

[75] Inventor: Robin G. Simmonds, Wokingham, England

[73] Assignee: Lilly Industries Limited, London, England

[21] Appl. No.: 325,513

[22] Filed: Nov. 27, 1981

[30] Foreign Application Priority Data

Dec. 4, 1980 [GB] United Kingdom ............... 8038910

[51] Int. Cl.$^3$ ............... C07C 107/06; C07C 113/04; C09B 29/12; C09B 33/044
[52] U.S. Cl. ............................ 260/149; 260/148; 260/174; 260/178; 260/184; 260/186; 260/187; 260/206; 260/207; 260/141
[58] Field of Search ............... 260/206, 207, 184, 174, 260/178, 186, 187, 148, 149

[56] References Cited

U.S. PATENT DOCUMENTS 2,993,886  7/1961  Weis et al. ........................ 260/163
4,118,383 10/1978  Botros ............................... 260/156

OTHER PUBLICATIONS

Wofsy & Henry, *Contemporary Topics in Molecular Immunology*, 7, 215 (1978), Plenim Press.

Cammisuli & Wofsy, *J. Immun.*, 117, 1695 (1976).

*Primary Examiner*—Floyd D. Higel
*Attorney, Agent, or Firm*—James L. Rowe; Arthur R. Whale

[57] ABSTRACT

Compounds of formula (I)

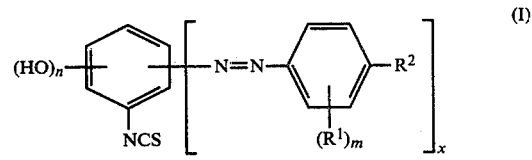

in which n is 1 or 2, $R^1$ is $C_{1-4}$ alkyl, $C_{1-4}$ alkoxy, nitro, amino, halo or hydroxy, m is 0, 1 or 2, $R^2$ is an immunogenic determinant and x is 1 or 2, provided that when n is 1, x is 1 or 2 and there is one diazo moiety at the 3-position or two diazo moieties at the 3- and 5-positions, with respect to the isothiocyanate group, and the hydroxy group is at the 4-position; and provided that when n is 2, x is 1 and the diazo moiety is at the 4-position and the hydroxy groups are at the 3- and 5-positions, are described. The compounds are useful in the preparation of immunoglobulin conjugates for employment in diagnostic techniques.

3 Claims, No Drawings

ISOTHIOCYANATO-AZOBENZENE-SULFONIC, ARSONIC AND SUBSTITUTED-GLUTAMIC ACID HAPTENS

This invention relates to novel compounds and their use in the preparation of novel hapten-immunoglobulin conjugates.

Techniques of studying antigen distribution in cell and tissue section preparations for the purpose of diagnosis are well known. Antibodies suitably marked with, for example, fluorescent material bind to antigen on the cell surface which is thus conveniently labelled. In one technique by indirect labelling, a second-layer antibody coupled to a suitable marker is employed to label a first-layer antibody specific for a particular antigen. The first-layer antibody can be modified by covalent linkage with one or more hapten molecules to form a hapten-antibody conjugate which in turn is detected by labelled antihapten antibody, see review by Wofsy L., Henry C. and Cammisuli S. in Contemp. Top. Mol. Immunol. 7.215. Such a labelling technique can also be applied to other immunoglobulin materials which may find utility in assay and control experiments.

In preparing the hapten-immunoglobulin conjugate it is, of course, important that the antibody or other immunoglobulin material, should not be seriously damaged and attachment of hapten is best effected by means of a reagent consisting of a hapten linked to a suitable coupling group.

The present invention provides a novel reagent which is conveniently prepared and readily handled and which can be employed under mild conditions to prepare hapten-immunoglobulin conjugates without appreciable loss of utility. The reagent of the invention is a compound of the formula (I)

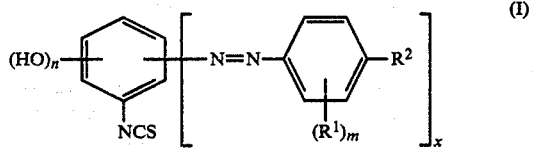

(I)

in which n is 1 or 2, $R^1$ is $C_{1-4}$ alkyl, $C_{1-4}$ alkoxy, nitro, amino, halo or hydroxy, m is 0, 1 or 2, $R^2$ is an immunogenic determinant and x is 1 or 2; provided that when n is 1, x is 1 or 2 and there is one diazo moiety at the 3-position or two diazo moieties at the 3- and 5-positions, with respect to the isothiocyanate group, and the hydroxy group is at the 4-position; and provided that when n is 2, x is 1 and the diazo moiety is at the 4-position and the hydroxy groups are at the 3- and 5-positions. The compounds of the invention are thus mono or bis azo derivatives of 4-hydroxy- or 3,5-dihydroxy-phenylisothiocyanate.

In the above formula (I), $R^2$ can be any suitable immunogenic determinant optionally in its various optical or racemic forms, and for example includes an arsonate group ($-AsO_3H_2$), a sulphonate group ($-SO_3H$), a nitro group ($-NO_2$), a carboxyl group ($-CO_2H$), a trimethylammonium group ($Me_3N-$) a group derived from glutamic acid

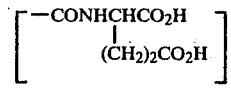

or a group derived from glycine [$-CONHCH_2CO_2H$] the preferred groups being arsonate, sulphonate and the groups derived from glutamic acid and glycine. The group $R^1$ when it is $C_{1-4}$ alkyl can be straight or branched chain and can be for example methyl, ethyl, propyl, isopropyl or butyl and is preferably methyl. When $R^1$ is $C_{1-4}$ alkoxy it is a $C_{1-4}$ alkyl group linked via an oxygen atom to the phenyl nucleus, and is preferably methoxy. When $R^1$ is halo it can be chloro, bromo or iodo and is preferably chloro. The most conveniently obtainable compounds are those in which m is o and a preferred group of components is one of the following formula:

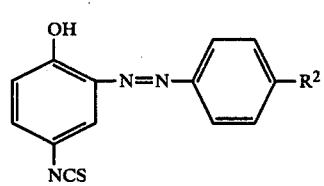

The invention also includes a method of preparing a compound of formula (I) which comprises reacting a phenylisothiocyanate of formula

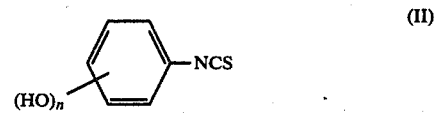

(II)

in which n is 1 and the hydroxy group is at the 4-position or n is 2 and the hydroxy groups are at the 3- and 5-positions, with a diazonium salt of formula

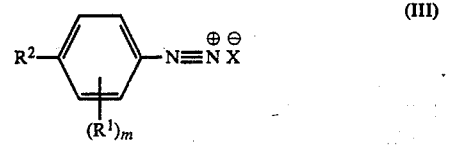

(III)

in which $R^1$, m and $R^2$ are as defined for formula (I) and $X^\ominus$ is an anion.

Reactants of formulae (II) and (III) are either known compounds or can be prepared from known compounds by simple chemical methods well known in the art. For example, the starting materials of formula (III) are prepared from arsanilic acid, p-aminobenzoyl glutamic acid, sulphanilic acid or derivatives thereof, which are readily diazotised by well recognized methods, employing for example sodium nitrite and dilute hydrochloric acid, to give the appropriate diazonium salt. The anion $X^\ominus$ is preferably a halid ion, for example chloride.

Compounds (II) and (III) are preferably reacted together in an aqueous medium at a temperature of from 0° C. to 5° C., the pH being maintained at from 8 to 10, for example at pH 9. If desired a water miscible solvent such as dimethyl formamide or tetrahydrofuran can be added, and the products of the process can be purified by recrystallisation or by gel filtration.

The compounds of the invention are convenient reagents that can be easily prepared. They are solids which are readily purified and prepared in high yield. In these respects they represent an improvement over prior art materials. Moreover they can be reacted under mild conditions with antibody to produce hapten-antibody conjugates with high yield and without significantly affecting the net charge or other physical properties of the antibody as to alter its binding activity.

The invention also provides a hapten-immunoglobulin conjugate which is an immunoglobulin modified with one or more, for example 5 to 20, groups of the formula

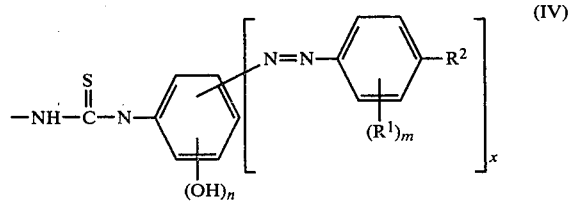

(IV)

in which n, $R^1$, m, $R^2$ and x have the values defined in formula (I); and a process for preparing a hapten-immunoglobulin conjugate which comprises reacting an immunoglobulin with a compound of formula (I). Preferably the immunoglobulin is an antibody.

The antibodies are obtained by well known procedures from the serum of immunised animals or by culturing hybridomas secreting monoclonal products.

Antibodies can be haptenated according to this method under mild conditions of pH and temperature with chemical modification occurring solely at free amino groups. For example the reaction can be effected at a temperature of from 10° C. to 25° C. such as at room temperature, in a suitable aqueous medium buffered to a pH of between 7.5 to 8.6. The resulting conjugate can be purified by gel filtration and stored in saturated ammonium sulphate solution, being readily brought back into solution by dialysis employing, for example, borate buffer or, alternatively, it can be stored in a refrigerator at 4° C. or frozen at for example −20° C.

The reaction results in one or more molecules of formula (I) being attached to the immunoglobulin and the number of molecules attached on the conjugate depends on the concentrations of the reactants employed and the time for which the reaction is allowed to proceed. Evaluation of the conjugate can be carried out using techniques such as affinity chromatography, determination of cytotoxicity and labelling specificity. The hapten concentration in solutions of conjugates can be determined by spectroscopy at pH 13, making use of pre-determined molar extraction coefficients at pH 13 of compounds of formula (I).

As has been indicated above, the hapten-antibody conjugates of the invention are employed in conjunction with labelled antihapten antibodies. These are easy to prepare and can be purified readily by affinity chromatography (Cuatrecases and Anfinsen, Methods in Enzymology, 34, 345 et seq., Academic Press, New York)

This system of indirect labelling can be used to discriminate between two antigens on the same cell or between two cells with distinguishing antigens. The procedure is especially suited to a situation in which each of two antigens is best visualized by the indirect method, since this can be done by the use of two non-crossreactive antihapten antibodies and for example antibodies with different fluorochromes can be used to distinguish clearly a variety of antigens on human and animal cell surfaces. This procedure is also suited to situations where increased sensitivity is required, by making use of the greater amplification achieved by using highly heptenised antibody.

Examples of preferred antibody for use in the immunoglobulin conjugates of the invention include anti-human Ig, anti-human Ia, anti-human Leu-1, anti-human T-cell markers, and anti-mouse Thy 1,2.

The invention is illustrated by the following Examples.

EXAMPLE 1

Preparation of 2-hydroxy-5-isothiocyanato-azo-benzene-4'-arsonic acid

Sodium nitrite (69 mg, 1 mmole) in water (1.5 ml) was added dropwise to a cooled (<5° C.) solution of arsanilic acid (217 mg. 1 mmole) in 1 N HCl (2.5 ml) and the mixture stirred at <5° C. for 30 minutes.

0.34M Borate buffer, pH 9.3(10 ml) was added to a solution of p-hydroxyphenylisothiocyanate (151 mg, 1 mmole) in DMF (2 ml) and the resulting emulsion cooled to 5° C. The diazonium solution was added dropwise with stirring at <5° C. over 5 minutes, the pH being maintained at pH 9±0.2 by the addition of <5 N NaOH. The reaction mixture was stirred at room temperature for 1 hour, then washed with ether (2×20 ml) and acidified to pH 1. The precipitated crude product was washed with 1 N HCl (20 ml) and water (20 ml), and redissolved in 0.1 M borate buffer pH 8.6 (5 ml). This solution was chromatographed at 4° C. on a 1.5×112 cm (200 ml) column of Bio-Gel P-2 (100–200 mesh) equilibrated with 0.1 M borate buffer pH 8.6. Fractions (8 ml) were collected and assessed by 600–400 nm scans aliquots diluted 1:30 with water. Fractions 17–24 were combined and acidified (pH-1), and the precipitated product washed with water (2×15 ml), suspended in water and freeze dried. λmax(0.1 N NaOH) 505 nm (8900)(m.p.>260° C.)

The following compounds were similarly prepared 2-Hydroxy-5-isothiocyanato-azo-benzene-4'-sulphonic acid (from sulphanilic acid), λmax(0.1 N NaOH) 510 nm (ε9100)(m.p.>260° C. L-2-(2-hydroxy-5-isothiocyanato-azo-benzene-4'-carboxamido)-glutaric acid (from L-p-aminobenzoylglutamic acid), λmax(0.1 N NaOH) 510 nm(ε10900). (m.p. 98° C.).

EXAMPLE 2

Preparation of L-benzoyl-glutamic acid-conjugated mouse IgG₂ anti-human Ia

100 μl of a solution of L-2-(2-hydroxy-5-isothiocyanato-azo-benzene-4'-carboxamido)-glutaric acid (4 mg/ml 0.34 M borate buffer pH 8.6 ) was added to a solution of mouse IgG₂ anti-human Ia(2.8 mg) in the same buffer (0.4ml). The mixture was stored in the dark at room temperature for 18 hours, then chromatographed on a 1.0×16.5 cm (13 ml) column of Biogel P-6 (supplied by Bio-Rad Laboratories Limited) equilibrated with buffer. The excluded peak (2.4 ml) was collected, and contained 1.2 mg/ml of conjugate having 8.2 moles L-benzoylglutamic acid/mole of antibody.

EXAMPLE 3

Preparation of arsanilic acid-conjugated mouse IgG$_1$anti-carcino-embryonic antigen 120 μl of a solution of 2-hydroxy-5-isothiocyanato-azo-benzene-4'-arsonic acid (4 mg/ml 0.34 M borate buffer pH 8.6) was added to a solution of mouse IgG$_1$ anti-carcinoembryonic antigen (4 mg) in the same buffer (0.5 ml). The mixture was stirred in the dark at room temperature. After 6 hours a 0.25 ml aliquot was chromatographed on a 1.0×15.5 cm (12 ml) column of Ultrogel AcA-54 (LKB Instruments Ltd) equilibrated with buffer. The excluded peak (2.8 ml) was collected and contained 0.6 mg/ml of conjugate having 8.8 moles arsanilic acid/mole of antibody.

After 24 hours the remainder of the reaction mixture was similarly chromatographed. The excluded peak (3.4 ml) contained 0.6 mg/ml of conjugate having 15.2 moles arsanilic acid/mole of antibody.

I claim:

1. A compound of formula

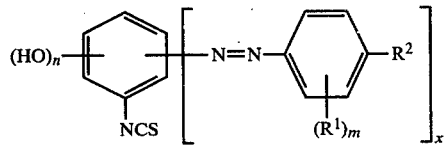

in which n is 1 or 2, $R^1$ is $C_{1-4}$ alkyl, $C_{1-4}$ alkoxy, nitro, amino, halo or hydroxy, m is 0, 1 or 2, $R^2$ is an immunogenic determinant and x is 1 or 2, provided that when n is 1, x is 1 or 2 and there is one diazo moiety at the 3-position or two diazo moieties at the 3- and 5-positions, with respect to the isothiocyanate group, and the hydroxy group is at the 4-position; and provided that when n is 2, x is 1 and the diazo moiety is at the 4-position and the hydroxy groups are at the 3- and 5-positions, wherein the term diazo moiety represents

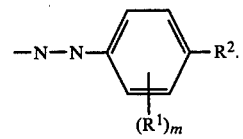

2. A compound according to claim 1 in which the immunogenic determinant is an arsonate (—As$O_3H_2$) group, a sulphonate group (—SO$_3$H) or

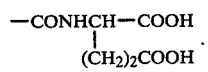

3. A compound according to either of claims 1 or 2 in which n is 1, x is 1 and m is o.

* * * * *